US008859003B2

(12) United States Patent
Akashe et al.

(10) Patent No.: US 8,859,003 B2
(45) Date of Patent: Oct. 14, 2014

(54) PREPARATION OF AN ENTERIC RELEASE SYSTEM

(75) Inventors: Ahmad Akashe, Mundelein, IL (US); Anilkumar Ganapati Gaonkar, Buffalo Grove, IL (US); Les Lawrence, Plainfield, IL (US); Amado R. Lopez, Chicago, IL (US); George W. Haas, Mount Prospect, IL (US); Dana Sebesta, Plano, IL (US); Yan Wang, Glenview, IL (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 0 days.

(21) Appl. No.: 12/976,614

(22) Filed: Dec. 22, 2010

(65) Prior Publication Data

US 2011/0159103 A1  Jun. 30, 2011

Related U.S. Application Data

(63) Continuation-in-part of application No. 12/479,454, filed on Jun. 5, 2009, now abandoned.

(51) Int. Cl.
| | | |
|---|---|---|
| *A61K 9/16* | (2006.01) | |
| *A61K 9/00* | (2006.01) | |
| *A61K 31/045* | (2006.01) | |
| *A61K 8/92* | (2006.01) | |
| *A23L 2/39* | (2006.01) | |
| *A61K 31/31* | (2006.01) | |
| *A61Q 13/00* | (2006.01) | |
| *A61K 31/015* | (2006.01) | |
| *A61K 31/05* | (2006.01) | |
| *A23L 1/22* | (2006.01) | |
| *A61K 8/11* | (2006.01) | |
| *A61K 9/50* | (2006.01) | |
| *A61K 8/64* | (2006.01) | |
| *A23L 2/52* | (2006.01) | |
| *A23L 1/00* | (2006.01) | |

(52) U.S. Cl.
CPC ............. *A61K 9/0095* (2013.01); *A61K 31/045* (2013.01); *A61K 8/927* (2013.01); *A23L 2/39* (2013.01); *A61K 31/31* (2013.01); *A61Q 13/00* (2013.01); *A61K 31/015* (2013.01); *A61K 2800/412* (2013.01); *A61K 31/05* (2013.01); *A23L 1/22016* (2013.01); *A61K 8/11* (2013.01); *A61K 9/5015* (2013.01); *A61K 9/5052* (2013.01); *A61K 8/645* (2013.01); *A23L 2/52* (2013.01); *A23L 1/0032* (2013.01)
USPC ........... 424/491; 424/757; 424/490; 424/755; 427/2.21; 514/546; 514/552; 264/4

(58) Field of Classification Search
CPC ......... A61K 31/31; A61K 8/11; A61K 8/645; A23L 1/0032; A23L 1/22016; A23L 2/39; A23L 2/52; A61Q 13/00

USPC ................. 424/491, 757, 490, 755; 427/2.21; 514/546, 552; 254/4
See application file for complete search history.

(56) References Cited

U.S. PATENT DOCUMENTS

| | | | |
|---|---|---|---|
| 2,464,204 A | | 3/1949 | Baker |
| 2,727,833 A | | 12/1955 | Yen et al. |
| 3,010,953 A | | 11/1961 | Unger et al. |
| 3,041,289 A | | 6/1962 | Katchen et al. |
| 3,116,206 A | * | 12/1963 | Brynko et al. ................ 424/491 |
| 3,869,406 A | | 3/1975 | Matsukawa et al. |
| 3,956,172 A | | 5/1976 | Saeki et al. |
| 4,518,458 A | | 5/1985 | Greenfield et al. |
| 4,601,863 A | | 7/1986 | Shioi et al. |
| 4,702,798 A | | 10/1987 | Bonanno |
| 4,778,781 A | | 10/1988 | Washizu et al. |
| 4,895,725 A | | 1/1990 | Kantor et al. |
| 4,936,916 A | | 6/1990 | Shinmitsu et al. |
| 5,051,304 A | | 9/1991 | David et al. |
| 5,051,305 A | | 9/1991 | Whitaker, Sr. |
| 5,146,758 A | | 9/1992 | Herman |
| 5,160,742 A | | 11/1992 | Mazer et al. |
| 5,164,210 A | | 11/1992 | Campbell et al. |
| 5,480,656 A | | 1/1996 | Okada et al. |
| 5,601,760 A | | 2/1997 | Rosenberg |
| 5,679,377 A | | 10/1997 | Bernstein et al. |
| 5,686,092 A | | 11/1997 | Lewis |
| 5,879,541 A | | 3/1999 | Parkinson |

(Continued)

FOREIGN PATENT DOCUMENTS

| | | |
|---|---|---|
| EP | 0 579 435 A1 | 1/1994 |
| EP | 0 827 997 A1 | 3/1998 |
| EP | 1 396 551 A1 | 3/2004 |
| EP | 1 721 605 A1 | 11/2006 |
| JP | 52-152876 A | 12/1977 |

(Continued)

OTHER PUBLICATIONS

Max S. Dunn and Howard B. Lewis, "The Action of Nitrous Acid on Casein," Journal of Biological Chemistry, vol. 49, 1921, pp. 327-341.

(Continued)

*Primary Examiner* — Suzanne Ziska
(74) *Attorney, Agent, or Firm* — Fitch, Even, Tabin & Flannery LLP

(57) ABSTRACT

Hydrophobic liquids are microencapsulated by an enteric matrix in an environment substantially free of organic solvents. The process includes forming an emulsion of the enteric material and hydrophobic liquid in water, titrating the emulsion with an acid to form a particulate precipitate and optionally coating the particulate with a combination of enteric material and plasticizer.

35 Claims, 7 Drawing Sheets

(56) References Cited

U.S. PATENT DOCUMENTS

| | | |
|---|---|---|
| 5,958,388 A | 9/1999 | Franks |
| 6,143,170 A | 11/2000 | Briggs et al. |
| 6,608,017 B1 | 8/2003 | Dihora et al. |
| 6,653,288 B1 | 11/2003 | Beuvry et al. |
| 6,770,285 B2 | 8/2004 | Keenan et al. |
| 6,921,539 B2 | 7/2005 | Ninkov |
| 6,923,988 B2 | 8/2005 | Patel et al. |
| 6,929,810 B2 | 8/2005 | Purohit et al. |
| 6,929,814 B2 | 8/2005 | Bouwmeesters et al. |
| 7,067,153 B2 | 6/2006 | Grisoni |
| 7,182,959 B2 | 2/2007 | Martani |
| 7,192,542 B2 | 3/2007 | Ugazio |
| 7,250,185 B2 | 7/2007 | Dowdle et al. |
| 7,279,495 B2 | 10/2007 | Ducray et al. |
| 7,338,928 B2 | 3/2008 | Lau et al. |
| 7,427,407 B2 | 9/2008 | Kume et al. |
| 7,541,155 B2 | 6/2009 | Enan |
| 7,585,538 B2 | 9/2009 | Mangos et al. |
| 7,622,269 B2 | 11/2009 | Enan |
| 2002/0055537 A1 | 5/2002 | Gerlach et al. |
| 2002/0173522 A1 | 11/2002 | Redmon et al. |
| 2002/0193452 A1 | 12/2002 | Brocker et al. |
| 2003/0082272 A1 | 5/2003 | Bouwmeesters et al. |
| 2003/0175403 A1 | 9/2003 | Gurin |
| 2003/0180369 A1 | 9/2003 | Grisoni |
| 2003/0203848 A1 | 10/2003 | Vertesy et al. |
| 2003/0225003 A1 | 12/2003 | Ninkov |
| 2003/0228369 A1 | 12/2003 | Kuhrts |
| 2004/0109894 A1 | 6/2004 | Shefer et al. |
| 2004/0191366 A1 | 9/2004 | Mangos et al. |
| 2004/0195711 A1 | 10/2004 | Hayashi et al. |
| 2004/0266888 A1 | 12/2004 | Ninkov |
| 2005/0014827 A1 | 1/2005 | Schur |
| 2005/0054682 A1 | 3/2005 | Phillips |
| 2005/0079138 A1 | 4/2005 | Chickering, III et al. |
| 2005/0100640 A1 | 5/2005 | Pearce |
| 2005/0123603 A1 | 6/2005 | Dalland et al. |
| 2005/0181059 A1 | 8/2005 | Jacob et al. |
| 2005/0200035 A1 | 9/2005 | Dobbs |
| 2005/0287276 A1 | 12/2005 | Lavoie et al. |
| 2006/0134282 A1 | 6/2006 | Mellema |
| 2006/0147503 A1 | 7/2006 | Floyd |
| 2006/0280795 A1 | 12/2006 | Penhasi et al. |
| 2007/0072944 A1 | 3/2007 | Gauvry et al. |
| 2007/0134332 A1 | 6/2007 | Turnell et al. |
| 2007/0141147 A1 | 6/2007 | Heil et al. |
| 2007/0145326 A1 | 6/2007 | Joseph et al. |
| 2007/0148198 A1 | 6/2007 | Joseph et al. |
| 2007/0190080 A1 | 8/2007 | Friedman |
| 2007/0218125 A1 | 9/2007 | Head et al. |
| 2008/0020078 A1 | 1/2008 | Enan |
| 2008/0029625 A1 | 2/2008 | Talton |
| 2008/0038362 A1 | 2/2008 | Park et al. |
| 2008/0125461 A1 | 5/2008 | Barberich |
| 2008/0145462 A1 | 6/2008 | Enan |
| 2008/0193531 A1 | 8/2008 | Hermelin et al. |
| 2008/0207766 A1 | 8/2008 | Devane |
| 2008/0226623 A1 | 9/2008 | Margolin et al. |
| 2008/0226649 A1 | 9/2008 | Schetter et al. |
| 2008/0226684 A1 | 9/2008 | Peppas |
| 2008/0255498 A1 | 10/2008 | Houle |
| 2008/0260819 A1 | 10/2008 | Fleming et al. |
| 2008/0299087 A1 | 12/2008 | Tseng et al. |
| 2009/0186096 A1 | 7/2009 | Kritzman et al. |
| 2009/0215892 A1 | 8/2009 | Nahab et al. |
| 2010/0310726 A1 | 12/2010 | Akashe et al. |
| 2011/0008471 A1 | 1/2011 | Enan |
| 2011/0020520 A1* | 1/2011 | Van Lengerich et al. ..... 426/546 |
| 2011/0124502 A1 | 5/2011 | Enan |
| 2012/0251641 A1 | 10/2012 | Enan et al. |

FOREIGN PATENT DOCUMENTS

| | | |
|---|---|---|
| JP | S63-197540 A | 8/1988 |
| JP | H02-103289 A | 4/1990 |
| JP | 04-330934 A | 11/1992 |
| JP | 05-017338 A | 1/1993 |
| JP | 08-026930 A | 1/1996 |
| JP | 10-273650 A | 10/1998 |
| JP | 2003-012526 A | 1/2003 |
| JP | 2004-018443 A | 1/2004 |
| JP | 2007-177129 A | 7/2007 |
| JP | 2008-013529 A | 1/2008 |
| RU | 2 098 121 C1 | 12/1997 |
| RU | 2 332 257 C2 | 3/2006 |
| SU | 339029 | 5/1972 |
| SU | 447163 A1 | 10/1974 |
| WO | 82/02496 A1 | 8/1982 |
| WO | 84/03201 A1 | 8/1984 |
| WO | 93/19622 A2 | 10/1993 |
| WO | 00/36924 A1 | 6/2000 |
| WO | 02/38181 A2 | 5/2002 |
| WO | 03/097015 A1 | 11/2003 |
| WO | 2005/082320 A1 | 9/2005 |
| WO | 2006/093838 A1 | 9/2006 |
| WO | 2007/044437 A2 | 4/2007 |
| WO | 2007/094000 A2 | 8/2007 |
| WO | 2008/003996 A1 | 1/2008 |
| WO | 20091117623 A2 | 9/2009 |

OTHER PUBLICATIONS

L. K. Ramachandran and W. B. McConnell, "The Action of Sulphuric Acid on Gliadin: With Special Reference to the N-Peptidyl→O-Peptidyl Bond Rearrangement," Canadian Journal of Chemistry, vol. 33, 1955, pp. 1638-1648.

R. M. Allison et al., "Notes on a deamination method proposed for determining 'chemically available lysine' of proteins," British Journal of Nutrition, vol. 29, 1973, pp. 51-55.

J. W. Paulis, "Disulfide Structures of Zein Proteins from Corn Endosperm," Cereal Chemistry, vol. 58, No. 6, 1981, pp. 542-546.

Microencapsulation of Food Ingredients, Edited by Per Vilstrup, Leatherhead Food RA Publishing, 2001, pp. 5-6.

LinShu Liu et al., "Pectin/Zein Beads for Potential Colon-Specific Drug Delivery: Synthesis and in Vitro Evaluation," 2006a, vol. 13, pp. 417-423.

PCT International Searching Authority International Search Report and Written Opinion for International Application No. PCT/US2011/065828 dated May 23, 2012, 11 pages.

C. L. Kruger and S.W. Mann, Safety evaluation of functional ingredients, Food and Chemical Toxicology, vol. 41, No. 6, Jan. 1, 2003, pp. 793-805, XP009144244, Pergamon, Great Britain.

Claudia S. Leopold and David R. Friend, "In vitro study for the assessment of poly(L-aspartic acid) as a drug carrier for colon-specific drug delivery," International Journal of Pharmaceutics, vol. 126, 1995, pp. 139-145.

European Patent Office Extended European Search Report for European Application No. 10251026.0 dated Aug. 30, 2010 (7 pages).

European Patent Office Extended European Search Report for European Application 10251044.3 dated Feb. 21, 2011 (6 pages).

Intellectual Property Office of New Zealand Examination Report dated Jun. 1, 2010 for New Zealand Application 585723, 3 pages.

Intellectual Property Office of New Zealand Examination Report dated Jun. 2, 2010 for New Zealand Application 585724, 3 pages.

Intellectual Property Office of New Zealand Examination Report dated Jun. 2, 2010 for New Zealand Application 585725, 3 pages.

L. R. Salgueiro et al., "Chemical Composition and Antifungal Activity of the Essential Oil of *Origanum virens* on *Candida* Species," Planta Med, vol. 69, 2003, pp. 871-874.

M. A. Del Nobile et al., Antimicrobial efficacy and release kinetics of thymol from zein films, Journal of Food Engineering, vol. 89, No. 1, Nov. 1, 2008, pp. 57-63, XP022704837, Barking, Essex, Great Britain.

(56) References Cited

OTHER PUBLICATIONS

Nicholas Parris et al., Encapsulation of Essential Oils in Zein Nanospherical Particles, Journal of Agricultural and Food Chemistry, vol. 53, Jun. 15, 2005, pp. 4788-4792, XP-002599360, American Chemical Society, United States of America.

Parag Kolhe et al., "Preparation, cellular transport, and activity of polyamidoamine-based dendritic nanodevices with a high drug payload," Biomaterials, vol. 27, 2006, pp. 660-669.

Pavan Muttil et al., "Inhalable microparticles containing large payload of ani-tuberculosis drugs," European Journal of Pharmaceutical Sciences, vol. 32, 2007, pp. 140-150.

Sunil A. Agnihotri et al., "Recent advances on chitosan-based micro- and nanoparticles in drug delivery," Journal of Controlled Release, vol. 100, 2004, pp. 5-28.

PCT International Preliminary Report on Patentability dated Jun. 25, 2013 for International Application No. PCT/US2011/065828, 5 pages.

Ain Raal et al., "Content and composition of the essential oil of *Thymus serpyllum* L. growing wild in Estonia," Medicina (Kaunas), 2004, 40(8), 795-800.

SIDS Initial Assessment Report for SIAM 14 dated Mar. 2002, Linalyl Acetate CAS No. 115-95-7, http://www.chem.unep.ch/irptc/sids/OECDSIDS/115957, 57 pages.

Wikipedia entry for Lavender oil, 2013, http://en.wikipedia.org/wiki/Lavender_oil, 5 pages.

\* cited by examiner

Data Analysis for Samples From Examples 2, 4 and 5

|  | Alpha-Pinene wt % | Para-Cymene wt % | Linalool wt % | Thymol wt % | Oil wt % | Payload (not including Oil) wt % | Total Payload wt % |
|---|---|---|---|---|---|---|---|
| Example 2 | 0.59 | 5.6 | 2.5 | 14.1 | <0.01 | 22.8 | 22.8 |
| Example 4 | 2.1 | 8.1 | 2.5 | 8.0 | 7.8 | 20.7 | 28.4 |
| Example 5 | 0.75 | 2.8 | 1.0 | 8.2 | 7.4 | 12.8 | 20.2 |

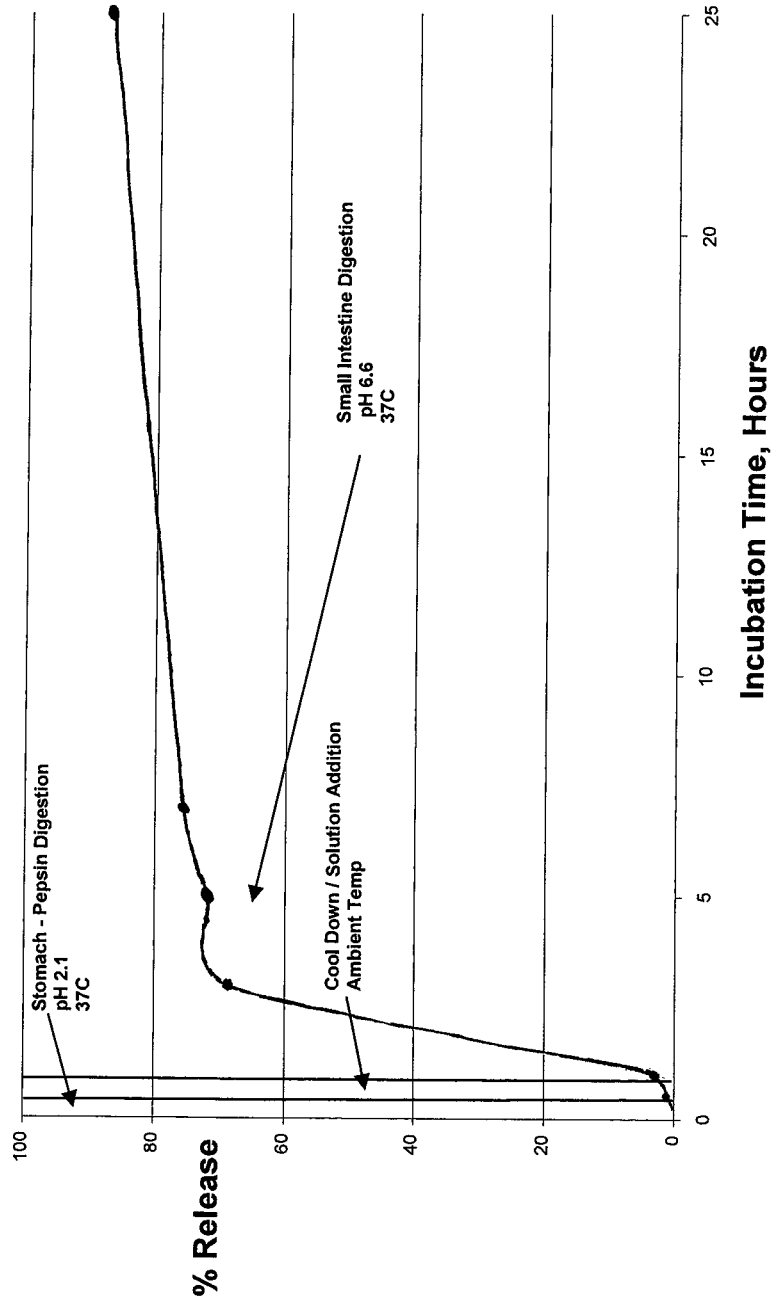

PREPARATION OF AN ENTERIC RELEASE SYSTEM

CROSS REFERENCE TO RELATED APPLICATIONS

This application is a continuation-in-part of U.S. patent application Ser. No. 12/479,454, filed Jun. 5, 2009, which is hereby incorporated by reference in its entirety herein.

FIELD

The present application relates to methods for microencapsulating a hydrophobic liquid with an enteric matrix substantially free of organic solvents. More particularly, the hydrophobic liquid is microencapsulated in an aqueous environment.

BACKGROUND

Enteric delivery of active materials in food delivery applications has been limited. Enteric delivery systems are commonly utilized when the active materials or medicaments are known to be sensitive to low pH or have undesirable flavor and/or taste characteristics which cannot be effectively masked by other methods. Generally, enteric delivery is accomplished using coated tablets and gel capsules. However, those particular delivery methods are not well suited for food applications. In particular, neither tablets nor capsules are sized to be integrated into most existing food products.

An alternative process for enteric delivery is microencapsulation. Enteric microencapsulation is generally performed using specialized equipment or in an environment including organic solvents. These methods require additional capital expenditures and the use of additional materials, such as the organic solvents, which may or may not be usable in subsequent microencapsulation cycles. As a result, the process of microencapsulation requires investments in both equipment and organic solvent procurement and disposal.

SUMMARY

A method is provided for microencapsulating an active ingredient(s) within an enteric matrix in an aqueous environment substantially free of organic solvents. Microencapsulating in an aqueous environment allows for easier working conditions and reduced organic waste.

A method is provided for microencapsulating an active ingredient with an enteric matrix. The method includes agitating or mixing a combination of water and an enteric material at a pH that forms an aqueous solution of the enteric material. The combination is substantially free of organic solvents. In one aspect, the enteric material is a combination of shellac and sodium caseinate. A hydrophobic liquid is then added to the combination. The hydrophobic liquid containing the active ingredients and combination is then agitated to create a coarse emulsion, followed by homogenization to create a fine and stable emulsion.

The emulsion can then be acid titrated with an amount of acid and at a rate effective to form a precipitate of a particulate of the hydrophobic liquid microencapsulated in the enteric matrix. Further, the particulate precipitate can be filtered, washed and dried to form a powder. In one embodiment a surface oil remover can be added to the precipitate after filtering to remove surface oil from the microencapsulated material.

In another aspect, one or more outer enteric coatings may be applied to the surface of the microencapsulated material. In one embodiment, the outer coating can include a combination of an enteric material and a plasticizer, such as a sugar alcohol (i.e., sorbitol). In another embodiment, the outer coating may be a combination of a first and second outer coating where the second outer coating can be applied after the first outer coating. The second outer coating may be provided from a combination of an enteric material and a plasticizer, such as a sugar alcohol, that may be the same or different from the first outer coating.

BRIEF DESCRIPTION OF THE FIGURES

FIG. 8 illustrates the release rate of the hydrophobic liquid in a simulated digestive system.

DETAILED DESCRIPTION

Figure 1:
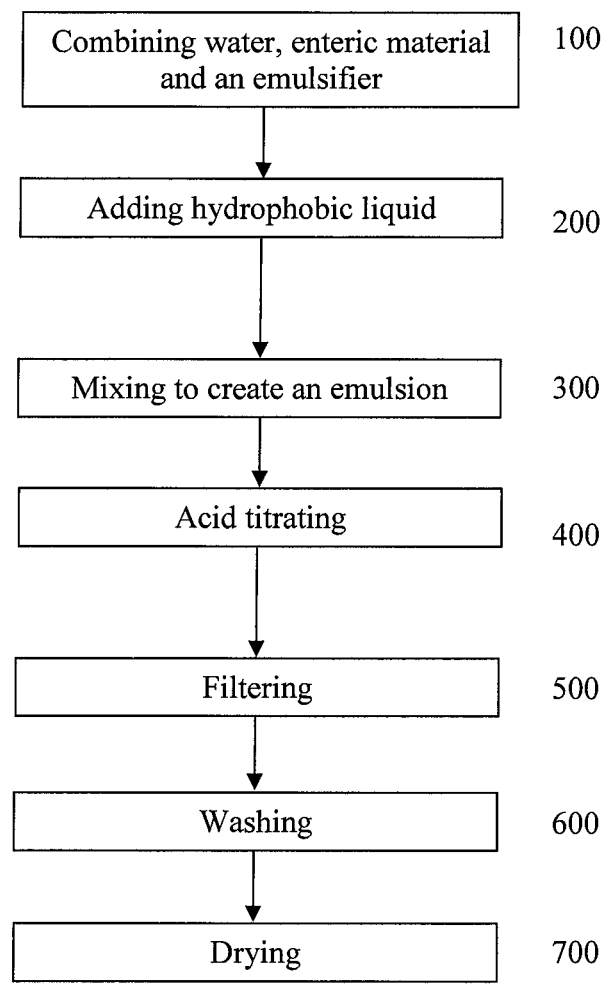
FIG. 1 illustrates a method for microencapsulating a hydrophobic liquid.

Methods are provided for microencapsulating a hydrophobic liquid in an aqueous environment substantially free of organic solvents. One method for microencapsulating a hydrophobic liquid is generally described in FIG. 1. As shown in FIG. 1, water, an enteric matrix material and an emulsifier are subjected to agitation until the enteric matrix material and emulsifier are combined with the water to form a solution 100. Generally, the emulsifier and enteric matrix material can be added to the water together or separately, with either being added first. In some cases, the pH of the solution is generally greater than 7, and generally greater than about 7.1 to about 9. In other cases, a base, such as sodium, ammonium or potassium hydroxide, can be added to the solution to maintain the pH greater than 7, and in yet other cases from greater than 7 to about 9 to maintain dissolution of the enteric polymers in water substantially free of organic solvents. The hydrophobic liquid is then added to the aqueous solution. The aqueous solution containing the hydrophobic liquid is then mixed to form an emulsion and then acid titrated to precipitate out the hydrophobic liquid microencapsulated with the enteric matrix material.

Figure 7:
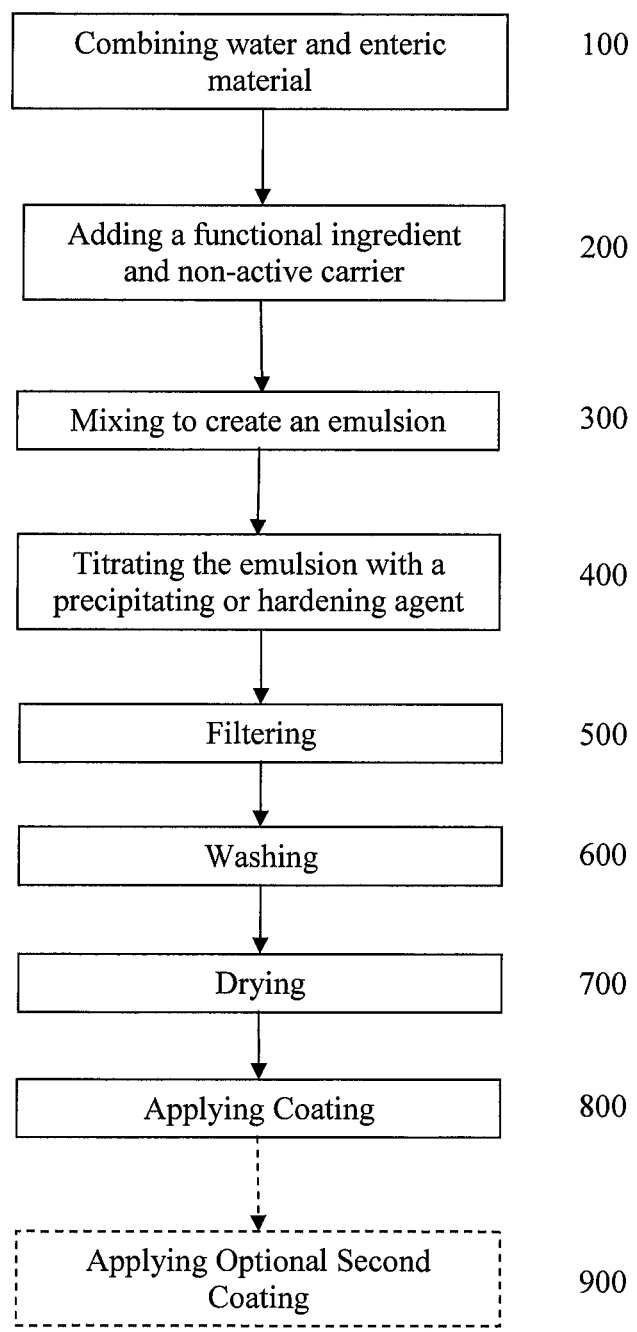
FIG. 7 is an illustration of an alternative method for microencapsulating a hydrophobic liquid.

Another method for microencapsulating a hydrophobic liquid is generally described in FIG. 7. This alternative method is similar to the methods of FIG. 1, but adds additional outer coatings of enteric materials. The methods of FIG. 7 are particularly suited to be used with enteric matrix materials of shellac and sodium caseinate with the optional inclusion of an emulsifier (both shellac and sodium caseinate provide emulsification). However, the methods of FIG. 7 may be used with other enteric matrix materials as well.

By one approach, "agitation" or "agitated" generally refers to the use of a top mixer with impeller or a rotor/stator mixing device operating at a speed of less than about 10,000 RPM. Other mixing devices may also be employed.

As used herein, "substantially free of organic solvent" generally refers to an amount of added organic solvent, such as isopropanol or ethanol or any other organic solvent, which is less than the amount of organic solvent required to enable solubilization of the enteric material under the processing conditions. Preferably, the amount of added organic solvent is less than about 0.1 percent by weight of the combination of water, emulsifier and enteric material. As used herein, "organic solvent" generally refers to a non-aqueous, hydrocarbon-based liquid.

In one embodiment, the water is deionized water.

The enteric matrix material used herein is any food grade enteric polymer, or a combination or two or more food grade enteric polymers. In one form, the enteric matrix material is either shellac or zein or a combination thereof. As discussed below, the ratio of enteric polymers, such as shellac to zein, can be predetermined to achieve the desired release rate after ingestion, with a decreased release rate corresponding with an increased ratio of shellac to zein. The shellac can be provided as an alkaline (pH>7) aqueous solution, such as a water-based solution having a solid content of about 25 percent by weight or it can be prepared from refined, bleached and dewaxed shellac powder. The shellac is substantially free of organic solvent, although it may contain trace amounts of organic solvents, such as isopropyl alcohol (such as can be included in commercial products), to act as a carrier for other ingredients in the shellac solution, such as methyl and propyl parabens. Preferably, the prepared shellac solution does not contain any added organic solvents.

In another form, the enteric matrix material includes a combination of shellac and zein, with zein comprising at least about 5 percent of the enteric matrix material by dry weight. Due to differences in hydration and solubility of zein and shellac, particularly the solubility at varying pHs and rates of hydration and solubility, different ratios of shellac to zein provide different enteric dissolution properties as well as differing degrees of core material protection in the final product, such as beverages.

In yet another form, the enteric matrix material may also include a combination of sodium caseinate and shellac. In one approach, the enteric matrix material consists essentially of shellac and sodium caseinate. The enteric matrix material and optional emulsifier may be solubilized in water, in one form alkaline water, substantially free of an organic solvent. However, it has been discovered that the combination of the solubilized shellac and sodium caseinate provides an emulsification capability so that the addition of an emulsifier is not required in this approach. Further, the combination of shellac and sodium caseinate improves stability of the resulting microencapsulated hydrophobic liquid over the duration of the shelf life of the microencapsulated hydrophobic liquid. In one approach, the enteric matrix material and sodium caseinate are solubilized separately in separate aqueous solutions and then combined in a single solution. In some cases, a desired ratio of shellac to caseinate ranges from about 90:10 to about 10:90, in other cases the ratio ranges from about 30:70 to about 70:30, and in yet other cases the ratio ranges from about 40:60 to about 60:40.

The emulsifier described herein is any food grade emulsifier. In one form, the emulsifier is polysorbate, polyglycerol ester, sucrose stearate, sucrose esters, proteins, lecithins or combinations thereof.

As described in more detail below, the methods herein combine water, an optional emulsifier, the enteric matrix materials and a hydrophobic liquid in a manner effective to microencapsulate the hydrophobic liquid in the enteric materials substantially free of organic solvents. Generally, the methods use water in amounts from about 50 percent to about 95 percent of the combination by weight and, in some approaches, from about 70 to about 95 percent, and, in other approaches, from about 80 to about 90 percent. The optional emulsifier is generally less than about 5 percent of the combination by weight, in some instances from about 0.01 to about 1 percent by weight, and, in other instances, about 0.01 to about 0.1 percent by weight of the combination. The enteric material ranges from about 3 percent to about 35 percent by weight, in some approaches from about 3 to about 23 percent, and, in other approaches, from about 10 percent to about 15 percent by weight of the combination. The hydrophobic liquid generally is in amounts of about 1 to about 15 percent by weight of the combination, and in other approaches, about 3 to about 6 percent by weight.

Turning back to FIG. 1, the water, enteric matrix material and optional emulsifier are combined 100 to form a solution. Upon forming the solution, a hydrophobic liquid is then added 200 to the combination and agitated to provide a coarse emulsion having a droplet size of more than about 10 micrometers. After the coarse emulsion is formed, the coarse emulsion is subjected to homogenization to create a fine, stable emulsion 300. The fine, stable emulsion has a droplet size of less than about 10 micrometers. Within the fine emulsion, the hydrophobic liquid is homogeneously dispersed in the form of fine droplets throughout. In one approach, the hydrophobic liquid is added in amounts ranging from about 1 to about 15 percent of the combination by weight. In other approaches, the hydrophobic liquid is added in an amount ranging from about 3 to about 6 percent of the combination by weight.

As used herein, "hydrophobic liquid" generally refers to any non-polar, water insoluble or immiscible liquid, such as essential oils, functional oils, oil solubles and any other functional material.

By one approach, "homogenization" or "homogenized" generally refers to the use of a rotor/stator mixing device operating at a speed greater than about 10,000 RPM or a valve homogenizer operating at a pressure of about 500 to about 10,000 psi. Other homogenization equipment may also be used.

The hydrophobic liquid can include any mixture of hydrophobic liquids and solids, such as solids mixed or combined therewith or dissolved or solubilized therein. As an example, hydrophobic liquid can be selected to include materials which are desired to be released in the small intestine rather than the stomach due to pH sensitivity. As an example, the hydrophobic liquid can include compositions described in U.S. Patent Publication No. 2008/0145462 to Enan. For instance, the hydrophobic liquid includes about 25 to about 35% by weight para-cymene, about 1 to about 10% by weight linalool, about 1 to about 10% by weight alpha-pinene, about 35 to about 45% by weight thymol, and about 20 to about 30% by weight soybean oil.

In particular, the hydrophobic liquid described herein can include an essential oil blend which possesses anti-parasitic properties. In one embodiment, the essential oil blend is organic compounds blended with food grade oil, i.e. soybean oil. Further, the organic compounds can include thymol and linalool. In a further embodiment, the organic compounds include alpha-pinene and para-cymene. As discussed in the examples below, one exemplary blend of an essential oil includes, by weight, about 17.5 percent soybean oil, about 8 percent alpha-pinene (liquid), about 44 percent para-cymene (liquid), about 5 percent linalool (liquid) and about 25.5 percent thymol (crystal). In another embodiment, the hydrophobic liquid may also include modified forms of the hydrophobic liquid, as described in provisional Patent Application Ser. No. 61/422,439, filed Dec. 13, 2010, which is incorporated herein in its entirety by reference. In yet another embodiment, the hydrophobic liquid includes esters, such as esters of linalool and thymol, as described in application Ser. No. 12/479,444, filed Jun. 5, 2009, which is incorporated herein in its entirety by reference.

Other suitable examples of a hydrophobic liquid include unsaturated and polyunsaturated OMEGA 3, other unsaturated and polyunsaturated lipids or fatty acids and triglycerides thereof, beta-carotene, and oil soluble vitamins, stomach irritants, or any other hydrophobic materials that are either sensitive to acidic pH conditions or impart strong undesirable taste.

Again turning back to FIG. 1, the fine, stable emulsion is then acid titrated 400. During acid titration, the emulsion is agitated. Acid is titrated in an amount effective to decrease the pH below the matrix solubility point, such as a pH of about 7, causing phase separation and inducing precipitation of the enteric matrix material out of solution with the hydrophobic liquid being microencapsulated therein, thus creating a slurry of an aqueous solution and precipitate. The slurry includes a particulate precipitate having a particle size from about 1 to about 1000 micrometers, in some cases about 10 to about 500 micrometers, and in yet other cases from about 75 to about 250 micrometers. In some approaches, precipitation occurs at a pH ranging from about 3 to about 6.5, and in other approaches from about 3 to about 5, and in one approach at a pH of about 4.5. In the method illustrated in FIG. 7, in order to maintain the enteric properties of the particulate precipitate, the fine, stable emulsion of sodium caseinate and shellac may be acid titrated to a pH corresponding to the insolubility at the isoelectric point of sodium caseinate, such as about 4.5 to about 4.6, which is below the solubility point of shellac. In some approaches, the slurry may be allowed to settle, resulting in a clear division of the liquid or supernatant and the settled particulate.

While not wishing to be limited by theory, it is believed that as the pH of the emulsion drops below the solubility point, enteric materials, such as shellac, sodium caseinate and zein, may cross-link to like particles or to one another to form a matrix, the hydrophobic liquid being microencapsulated within the matrix. As a result of the cross-linking, the hydrophobic liquid is homogeneously dispersed throughout the matrix. The matrix further provides a seal for the hydrophobic liquid. As a result, the impact of the hydrophobic liquid on the organoleptic qualities of the finished powder is generally correlated to any hydrophobic liquid remaining adhered to the outer surface of the enteric matrix.

The acid used for acid titration 400 can be any food grade acid. In one approach, the acid is a weak food grade acid. For example, the acid may be citric acid.

As noted above, the composition of the enteric matrix material affects the dissolution rate and the protection provided by the enteric matrix. As a result, the rate and amount of acid addition varies based on the enteric matrix materials used.

To reclaim the precipitate, the slurry may be filtered 500 to produce a wet cake, then washed 600 and dried 700 to produce a dried cake. In some approaches, both the particulate and the supernatant are both filtered 600 to produce a cake, then washed 600 and dried 700 to provide a dried cake. In another approach, the slurry or supernatant and particulate are filtered 600 to provide a wet cake. The wet cake is then washed, refiltered and rewashed prior to drying. In some approaches, the surface oil on the outer surface of the particulate precipitate is less than about 1 percent by weight of the final product.

In one embodiment, a surface oil remover may be added after filtering to aid in removing residual surface oil from the precipitate, as described in co-pending application Ser. No. 12/479,433, filed Jun. 5, 2009, which is incorporated herein in its entirety by reference. Further, the surface oil remover can also be added prior to the refiltering step.

After the precipitate has been filtered and washed, the precipitate is dried to form a powder. Drying can be conducted at room temperature such that the powder has a moisture content of less than about 10 percent, and in some cases to a moisture content of about 5 to about 6 percent.

Further, the powder can be pulverized to reduce the particle size of the powder precipitate, and then further dried to a moisture content of less than about 5 percent, such as with a fluidized bed dryer. By one approach, the resultant particles have a particle size ranging from about 1 to about 1000 micrometers, in some approaches from about 10 to about 500 micrometers, and in other approaches from about 75 to about 250 micrometers.

When drying the powder, the temperature may be maintained between about 25 C to about 70 C, in some approaches between about 35 C to about 60 C, and in other approaches between about 35 C and about 45 C. During other processing steps, the temperature may be maintained between about 4 C to about 40 C, in some cases about 4 C to about 30 C, and in other cases from about 15 C to about 28 C.

The microencapsulated hydrophobic liquid produced by the above described methods may have an increased payload. Payload generally refers to the weight percentage of the functional ingredients in relation to the final particulate product. The total payload generally refers to the total weight percentage of all the encapsulated functional ingredients, including the any carrier oil, in relation to the final particulate product. Therefore, an increase in payload corresponds to an increase in functional ingredient per a given amount of enteric matrix.

Turning to FIG. 7, the resultant powder can be further processed, such as applying an outer coating around the enteric matrix particulate product 800. The outer coating surrounds the enteric particulate product and any residual surface oil or functional ingredients on the surface of the particulate product. In some cases, the outer coating can improve the shelf life of the particulate product. The efficacy of the coating as a shelf life extender depends on many variables, including the enteric material used for providing the enteric matrix. In some cases, the application of an outer coating can increase the shelf life of particulate product where sodium caseinate is used as an enteric matrix material.

The outer coating can include any food grade enteric polymer, or can include a combination of food grade enteric polymers and a plasticizer such as a sugar alcohol (i.e., sorbitol). In some approaches, the outer coating may include a combination of two layers where a second outer coating 900 can be applied onto the first outer coating. The second outer coating may also be any food grade enteric polymer, or a combination of a food grade enteric polymer and a plasticizer, such as a sugar alcohol (i.e., sorbitol). The second outer coating may be the same or different form the first outer coating.

Each solution to prepare the first and second outer coatings can include about 5 percent to about 20 percent enteric material and about 1 percent to about 3 percent plasticizer, such as a sugar alcohol. The final, coated microencapsulated particles can include between about 1 to about 15 percent by weight of each of the first and second coatings.

The outer coating materials can be applied to the enteric matrix by mixing, spraying or other suitable application 800 and 900. (FIG. 7). In one approach, the outer coating materials are first solubilized in water. A base can optionally be added to the solubilized outer coating material to increase the pH to greater than 7, in some cases between about 7.1 and about 12. The solubilized material can then be atomized and sprayed onto the uncoated particulate product.

In one approach, the enteric matrix can be coated via two different coating steps 800 and 900. For example, the first coating step 800 includes atomizing a solution including zein and sorbitol to coat the uncoated enteric matrix. By one approach, the first coating material may include from about 1 percent to about 20 percent zein and from about 1 percent to about 3 percent sorbitol. The first coating material is solubilized in water, after which the pH is adjusted by adding a base material. For instance, an amount of a base, such as ammonium hydroxide, can be added to increase the pH in order to completely solubilize the zein, in some cases to a pH of about 9.5 to about 12. In some cases, the pH can then be increased in a two step addition by adding a second base material, such as sodium hydroxide. The solubilized coating material can then be atomized and sprayed into a fluidized bed coater to coat the uncoated enteric matrix particulate product within the fluidized bed.

In some instances, multiple coatings are advantageous. If used, the second coating step 900 may include atomizing a solution of enteric material and plasticizer to coat the uncoated particles. In some cases, the enteric material of the second coating is not the same as the enteric material of the first coating. For example, the second enteric material may be shellac and the plasticizer is sorbitol. By one approach, the second outer coating material includes from about 1 percent to about 20 percent shellac and from about 1 percent to about 3 percent sorbitol. The second coating material is then solubilized in water. The solubilized second coating material can then be atomized and sprayed into a fluidized bed coater to coat the once-coated enteric matrix particulate product within the fluidized bed. In some instances, the first and second coatings each have coating thicknesses of about 1 micrometer to about 5 micrometers. In some cases, the final particle size of the coated particle is about 1 to about 1000 micrometers, in other cases about 10 micrometers to about 500 micrometers, in other cases from about 50 micrometers to about 300 micrometers, and in yet other cases from about 75 micrometers to about 250 micrometers. If desired, the coated matrix particles can then be sieved to meet the desired particle size.

Advantages and embodiments of the methods described herein are further illustrated by the following Examples. However, the particular conditions, processing schemes, materials, and amounts thereof recited in these Examples, as well as other conditions and details, should not be contrasted to unduly limit this method. All percentages are by weight unless otherwise indicated.

EXAMPLES

Example #1

100 Percent Shellac as the Enteric Matrix Material

An essential oil blend was prepared by blending about 8 percent alpha-pinene (liquid), about 44 percent para-cymene (liquid), about 5 percent linalool (liquid), about 25.5 percent Thymol (crystal), and about 17.5 percent soybean oil. Mixing in a glass beaker with stirring bar was typically carried out until all of the Thymol crystals are dissolved.

In a large beaker the following steps were carried out in the order specified: about 1200 g of deionized (DI) water was added to the beaker, and then about 300 g of the stock solution of about 25 percent shellac (MarCoat solution from Emerson Resources Inc.) was mixed into the DI water under agitated conditions such that the pH of solution ranges from about 7.2 to about 9. While agitating, about 0.8 g of polysorbate 85 was added and mixed for about 1-2 minutes for full dispersion. Next, about 35 g of an essential oil blend was slowly added under agitated conditions to form a coarse emulsion. Once the oil was dispersed, the mix was homogenized at about 12500 rpm for about 5 minutes using Fisher Scientific PowerGen 700D Homogenizing System with 200 millimeter×25 millimeter Generator head.

The emulsion was then subjected to agitation and, while mixing, about 2 percent citric acid solution was titrated in at a slow rate while monitoring the resultant change in pH. Titration continued until the pH reached about 4.4, after which $SiO_2$ (AB-D from Pittsburgh Plate Glass Industries) was added (about 5 g $SiO_2$, in about 200 g water, and the slurry was mixed for about 15-20 minutes.

The slurry was then filtered by pouring the slurry over a 200 mesh screen with 75 micrometer holes. The particulates on the top of the screen were resuspended in about 1000 g water with about 3.5 g $SiO_2$. The slurry was mixed for about 30 to about 60 seconds and then re-filtered. The washing was repeated one more time as above, the filtrate was collected, spread on tray and allowed to dry at room temperature for overnight (to a moisture content of between about 5 to about 6 percent).

A sample was analyzed for percent Payload of each component and total. The payload generally refers to the weight percentage of the functional ingredients in relation to the final particulate product. The total payload generally refers to the total weight percentage of all the functional ingredients, including the soybean oil, in relation to the final particulate product. Therefore, an increase in payload corresponds to an increase in functional ingredient per a given amount of enteric matrix.

| | Alpha-Pinene % | Para-Cymene % | Linalool % | Thymol % | Soybean Oil % | Total Payload % |
|---|---|---|---|---|---|---|
| Payload | 0.7 | 3.2 | 1 | 7 | 5.6 | 17.5 |

Example 2

Illustrating Scalability and the Effect of an Oil Carrier Mixed with the Functional Ingredient Using 100 Percent Shellac as a Matrix Material About 12 kg of water was added to a mixing tank, with about 3 kg of a shellac solution (about 2 to about 5 percent shellac) then added and mixed with the water. The mixture was adjusted to a pH of about 8 by adding about 10 percent sodium hydroxide solution. About 5 g of sucrose stearate was then added and mixed for about 1-2 minutes, after which about 400 g of an essential oil blend without soybean oil (about 38.3% thymol, about 51.6% para-cymene, about 4.4% alpha-pinene and about 5.7% linalool) was slowly added. The mixture was homogenized as in Example 1 to prepare a stable emulsion.

Figures 2, 6:
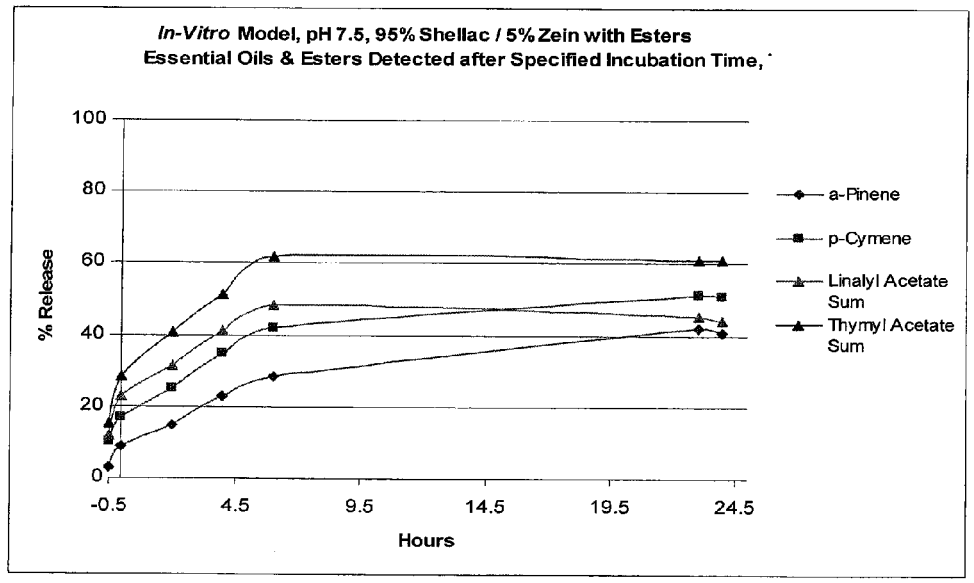
FIG. 2 is an analysis of the products of Examples 2, 4 and 5.
FIG. 6 illustrates the release rate of the hydrophobic liquid including esters therein as discussed in Example 7.

The emulsion was then titrated with about 2 percent citric acid solution until pH reached about 4.4, and then about 75 g of $SiO_2$ was added and mixed in for about 20 minutes. The slurry was then filtered using a 200 mesh (75 micrometer) screen. The filter cake was re-suspended in about 20 lb of water with about 50 g $SiO_2$, mixed for about 5 minutes, and then re-filtered on a 200 mesh screen. The washing was repeated one more time, and the final filter cake was spread on a large tray for overnight drying at room temperature (about 20 to about 25 C). The next day, the product was pulverized in a warring blender, and then fluid bed dried at about 40 C. Collected powder was sifted through a 35 mesh (500 micrometer) screen. FIG. 2 provides the compositional analysis.

Example #3

Use of 100 Percent Zein Powder (Corn Proteins) as the Enteric Matrix Material

About 75 g of zein (F4000 from Freeman Industries) powder and about 1200 g of DI water was combined in a large beaker. The zein was then dispersed in the water via agitation. Once the zein powder was completely dispersed, about 10 percent sodium hydroxide solution was slowly titrated into the dispersed zein until the pH reached about 11.3. At this pH, the zein powder was completely solubilized. Next, about 0.7 g of polysorbate 85 was added, agitated for about 1-2 minutes, and then about 30 g of the essential oil blend from Example 1 was added. The mixture was homogenized as in Example 1. The emulsion was then titrated with about 2 percent citric acid solution (as in Example 1) until pH reached about 4.6. The slurry was mixed for about 15-20 minutes.

Filtering and washing was conducted as in Example 1, except no SiO2 was added. Filtrate was collected and dried on a tray at room temperature for overnight. Sample was analyzed for percent payload of each component and total payload. The payload generally refers to the weight percentage of the functional ingredients in relation to the final particulate product. The total payload generally refers to the total weight percentage of all the functional ingredients, including the soybean oil, in relation to the final particulate product.

|  | Alpha-Pinene % | Para-Cymene % | Linalool % | Thymol % | Soybean Oil % | Total Payload % |
|---|---|---|---|---|---|---|
| Payload | 0.9 | 4.1 | 0.9 | 6.5 | 6.7 | 19 |

Example #4

Scalability of the Process Using 100 Percent Zein as the Enteric Matrix Material In a large mixing tank with a propeller overhead mixer, about 12 kg of water was added into the tank followed by about 10 g of sucrose ester (S-1570 from Mitsubishi Kagaku Corporation, Tokyo, Japan). The sucrose ester was then dispersed in the tank by agitation. Next, about 750 g of zein powder was dispersed via agitation in the tank, followed by metering of about 10 percent sodium hydroxide solution into the tank while mixing until pH reached about 11.3. The resulting solution was then mixed until the zein powder was completely dissolved. Next, about 400 g of the essential oil blend from Example 1 was slowly added. Once all the oil was dispersed, the mixture was homogenized for about 5 minutes to create an emulsion as in Example 1.

The emulsion was then titrated with about 2 percent citric acid solution under agitation until pH reached about 3.8. The slurry was allowed to mix for about an extra 10 minutes. The mixture was transferred into separate containers, allowed to stand for a few minutes so the precipitated particulates could settle at the bottom.

The supernatant was decanted onto a large 200 mesh screen followed by screening the remaining particulates. The filtrate on top of the screen was re-suspended in about 9 kg of acidified water (pH about 3.5), containing about 20 g SiO2, mixed for a few minutes and then decanted and filtered. This washing step was repeated one more time, the rinse water containing about 20 g SiO2, after filtering the filter cake was collected, spread thin on a tray and allowed to dry overnight at room temperature (about 20 to about 25 C). The semi-dry powder was pulverized and then fluid bed dried at about 40° C. to target moisture (less than about 5 percent). Final product was sifted through a 35 mesh (500 micrometer) screen. See FIG. 2 for the compositional analysis.

Example 5

Matrix Containing about 75 Percent Shellac & about 25 Percent Zein

Similar to example 4, about 12 kg of water and about 7.5 g of sucrose stearate (S-1570) was added to a mixing tank and mixed for about 1-2 minutes. Next, about 2.3 kg of about 25 percent shellac solution was added, followed by about 187.5 g zein powder. Next, about 10 percent sodium hydroxide was metered in until pH reached about 11.3 (to solubilize zein). Once the zein powder was completely in solution, about 400 g of the essential oil blend from Example 1 was added. The mixture was homogenized as in Example 1, and then the emulsion was titrated to pH about 3.9 with citric acid solution. About 75 g of SiO2 (Flow Guard AB-D) was then added and mixed for about 20-30 minutes. Filtering, washing, and drying processes were carried out in a similar fashion as described in example 4. Final powder was sifted through 35 mesh (500 micrometer) screen. See FIG. 2 for the compositional analysis.

Example #6

In Vitro Testing of Simulated Release in Stomach and Small Intestine

This example is intended to show the release rate and profile of actives from the matrix of the microcapsules from Examples 2, 4, and 5. Release from enteric microcapsule samples was evaluated by sequential simulation in a stomach simulation solution (about 10 mg/ml pepsin, about 2 mg/ml NaCl, pH about 2) for about 30 min followed by a small intestinal simulation solution (about 10 mg/ml pancreatin, about 2.4 mg/ml bile salt, pH about 6.8) for up to about 24 hr at about 37 C. Samples were taken at pre-determined time intervals and analyzed for release of individual actives.

Figure 3:
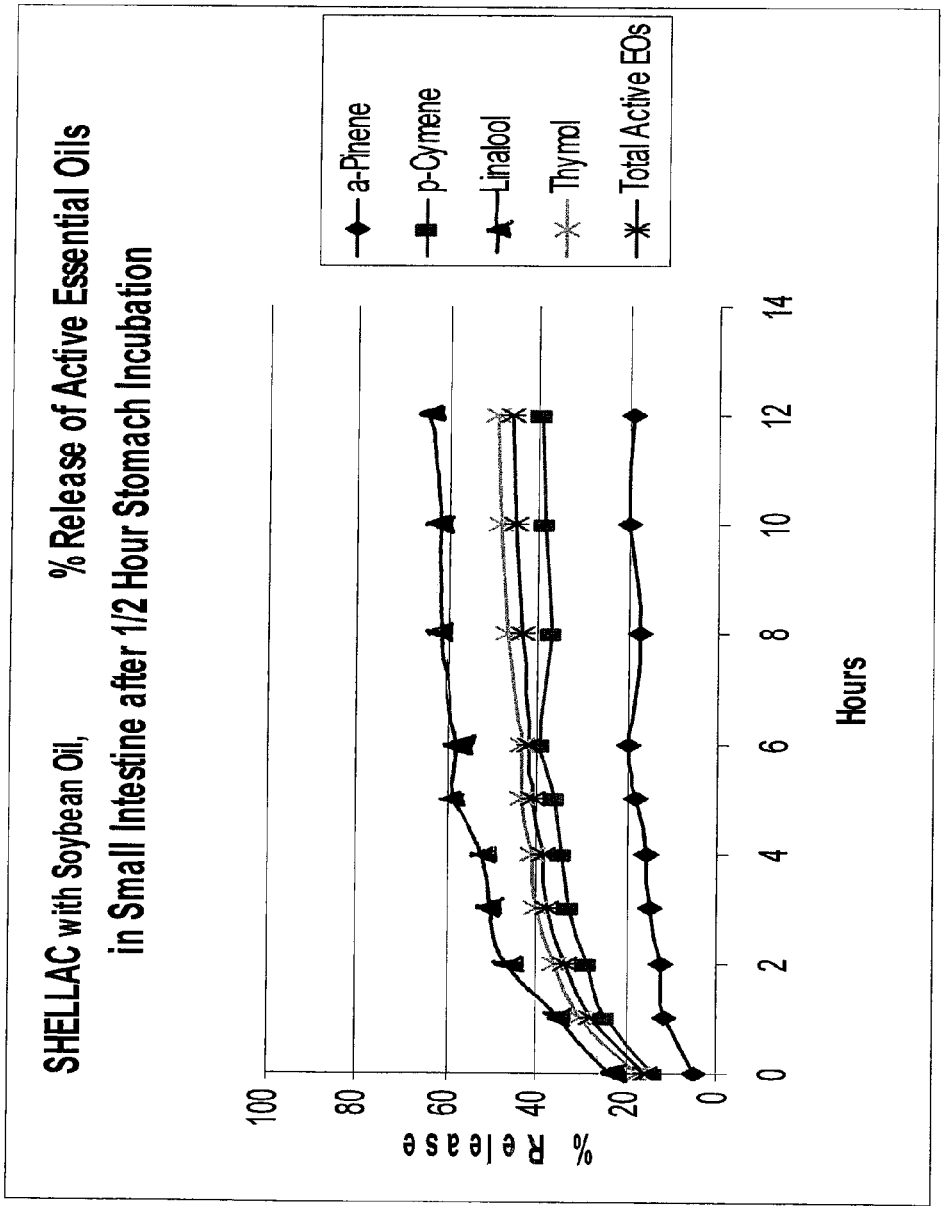
FIGS. 3-5 illustrate release rates of the hydrophobic liquid using various enteric matrix materials as discussed in Example 6.
Figure 4:
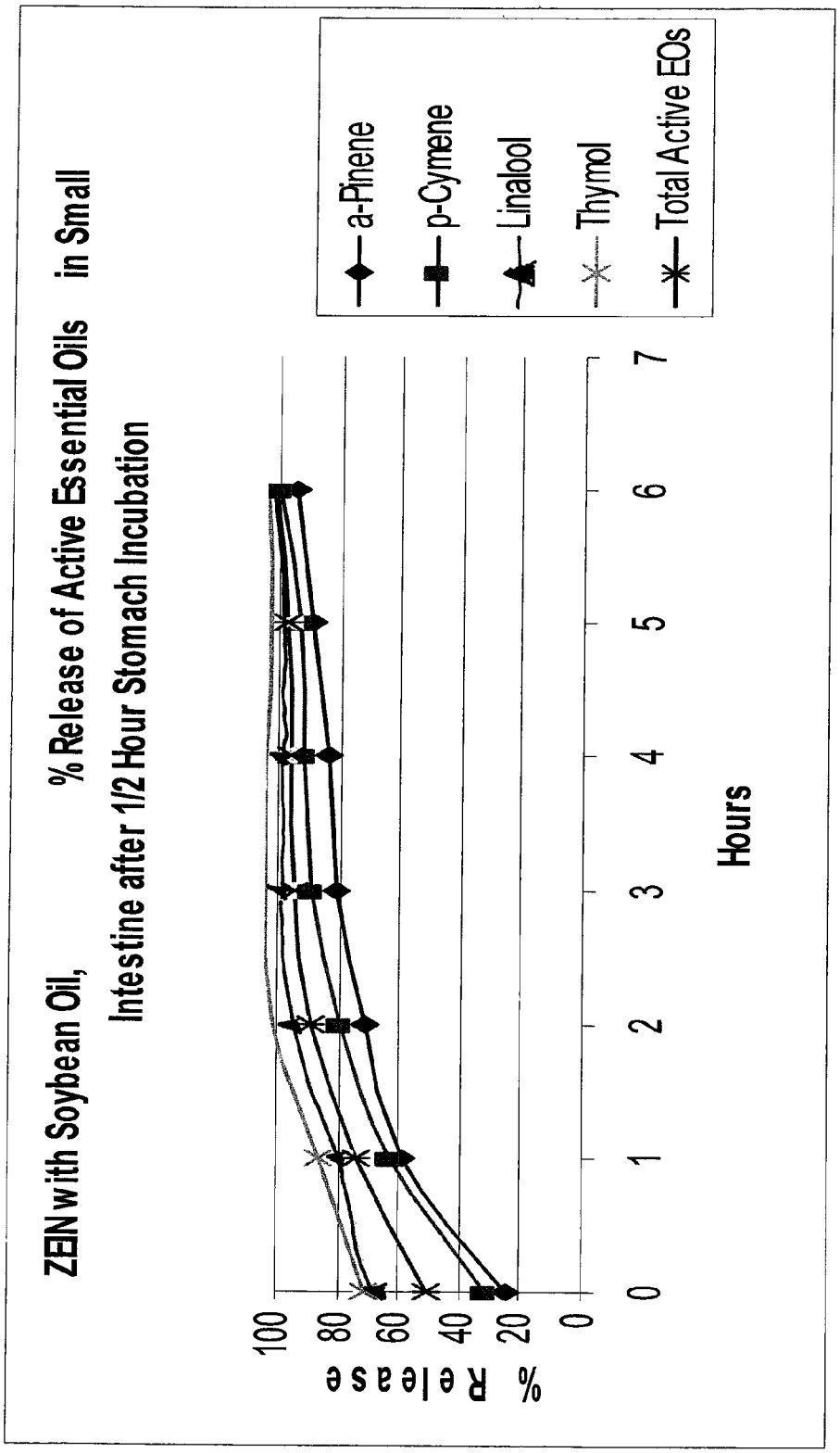
Figure 5:
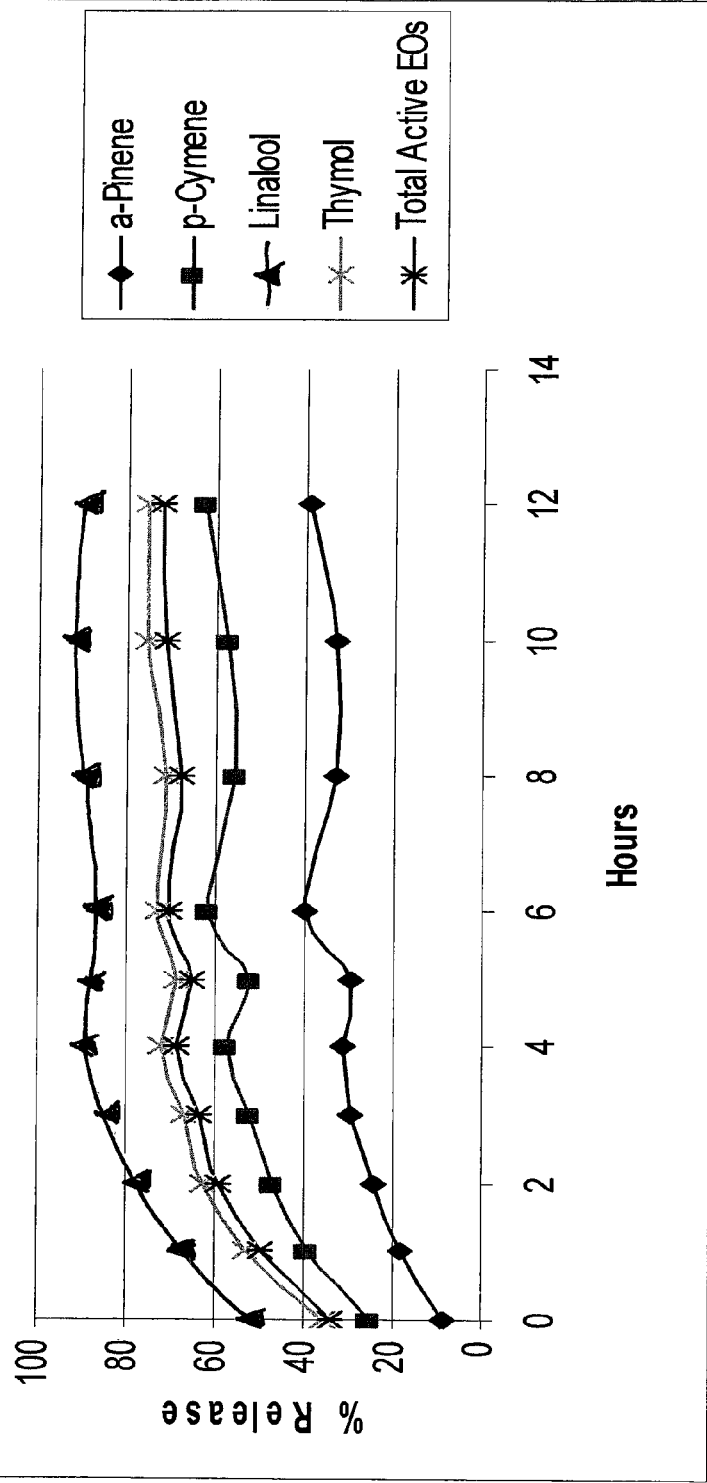

The release profile is different for the three compositions. When the matrix was made up of 100 percent shellac (as seen in FIG. 3), the release of the active materials from the essential oils continued to have a gradual increase over time but never reached complete release even after 12 hrs. On the other hand, the release can be characterized as having a quicker release rate and higher total release when the matrix is made up of 100 percent zein (about 80 percent of the total payload is released at the first hour in the intestinal conditions) (see FIG. 4). The combination of the shellac and zein (See FIG. 5) show a higher rate than 100 percent shellac, but lower than 100 percent zein, and the release seem to be sustained at a slow rate with a maximum after 6 hours.

Example #7

This Example Demonstrates the Microencapsulation of Oil Blend Containing Two Esterified Components (Thymol Acetate and Linalool Acetate in Combination with Alpha-Pinene, Para-Cymene, and Canola Oil)

In a beaker, about 2400 g of water was added and then, with agitated mixing, about 7.5 g of zein powder was dispersed in the water. About 10 percent sodium hydroxide solution was metered into the aqueous solution until pH reached about 11.3 (to solubilize the zein powder). Next, about 570 g of about 25 percent shellac solution and about 1 g sucrose stearate (S-1570) were added, followed by about 70 g of an essential oil blend (about 18.8 percent canola oil, about 8.6 percent alpha-pinene, about 39.8 percent para-cymene, about 5.4 percent Linalool acetate and about 27.4 percent Thymol acetate), which was added slowly to the mix. The emulsion was then homogenized (as in Example 1) using a Fisher Scientific PowerGen 700D Homogenizing System with 200 millimeter×25 millimeter Generator head at about 15000 rpm for about 4 minutes, then at about 20000 rpm for about 1 minute.

The emulsion was then titrated with about 3 percent citric acid solution to pH about 4. Then, about 280 g of about 10 percent sodium chloride solution and about 15 g SiO2 was added and allowed to mix for about 30 minutes. The slurry was then filtered and washed similar to that described in Example 1. The washed filter cake was spread on a tray to dry overnight, and then further dried in a fluid bed dryer at about 40 C, powder was sifted and product passing through 35 mesh (500 micrometers) size was collected. Final moisture was about 4.7 percent.

The release rate is shown in FIG. 6. In particular, while the overall release of the essential oil composition was not as high as in FIGS. 3-5, the initial release (through 1 hour) was lower than the compositions illustrated in FIGS. 3-5. Note that the payload generally refers to the weight percentage of the encapsulated functional ingredients and oil in relation to the final particulate product. The total payload generally refers to the total weight percentage of all the encapsulated functional ingredients and canola oil, in relation to the final particulate product.

|  | Alpha-Pinene % | Para-Cymene % | Linalool Acetate % | Thymol Acetate % | Canola Oil % | Total Payload % |
|---|---|---|---|---|---|---|
| Payload | 0.9 | 3.8 | 1.2 | 6.6 | 5.8 | 18.3 |

Example #8

Preparing Cream Wafer with Microencapsulated Essential Oil Wafer Filling

White cream filling was prepared by mixing in a Hobart mixer. First about 750 g of pre-melted San-Trans 39 Shortening plus about 0.5 g of liquid soy lecithin was mixed with confectionary sugar (powder sugar), until smooth and homogeneous. Filling was transferred into a container and cooled down for later use.

Wafer cracker sheets were purchased from local grocery store. About 97.8 g of cream filling was softened by warming up in a microwave oven. To the filling, the following was added: about 1.5 g of microencapsulated material, about 0.15 g citric acid, about 0.5 g Lemon oil flavor, one drop of beta-carotene for yellow color. The filling was spread on the cracker sheet (about 1-2 millimeters thick), and then another sheet was applied onto the top. The cracker sheet sandwich was then cooled in a refrigerator (about 0 to about 5 C) for about 30 minutes, and then it was cut to different sizes (cracker size). A similar formulation, double and triple layer crackers were also prepared. Other flavor varieties were also evaluated including chocolate and fruit flavors.

Example 9

Cracker Sandwich with Filling Including the Microencapsulated Material

A cracker sandwich with microencapsulated powder incorporated into the filling was prepared as follows:

Filling:
1) Fat portion: In a glass beaker, about 2000 g of Shortening San-Trans 39 was melted in microwave oven for about 3 minutes until it became a clear liquid, after which about 0.8 g of soy lecithin was added.
2) Solid blend portion: In a Hobart mixer, the following was dry blended: about 100 g lactose, about 10 g salt, and about 249.4 g Maltodextrin (5 D.E.).

The melted fat was poured onto the dry blend in the Hobart Mixer, and allowed to mix for at least about 5 minutes (to form a homogeneous mix). The filling was transferred into a container and used as a stock filling.

Cracker sandwich: about 100 g of cheese filling was warmed up in a microwave oven for about 30 seconds and to the softened filling, about 1.4 g of the microencapsulated material was mixed in, and also various seasoning and flavor blends. About 18 g of the filling was sandwiched between two crackers, and allowed to cool down. Different flavor varieties of cracker sandwiches were evaluated including, nacho, taco, Italian herb, and oriental seasoning. Filling was also evaluated with different type of crackers, including Saltine, Ritz and others. When evaluated, the crackers containing microencapsulated essential oil were pleasantly acceptable.

Example 10

This Example Demonstrates the Encapsulation of the Essential Oils, Followed by Surface Oil Removal as Disclosed in Co-Pending application Ser. No. 12/479,433

In a beaker, about 2400 g of water was added in and then, with overhead low shear mixing, about 37.5 g of zein powder was added and dispersed throughout the water. Next, about 10% sodium hydroxide solution was metered into the aqueous solution until pH reached about 11.3 (to solubilize the zein powder). Next, about 450 g of 25% shellac solution was added, followed by about 1.4 g sucrose stearate (S-1570), and then about 80 g essential oil blend (about 13% canola oil, about 10% alpha-pinene, about 25% Para-cymene, about 12% Linalyl acetate, about 40% Thymol acetate) was added slowly to the mix. The emulsion was then homogenized using an IKA Works T25 Basic Ultra Turrex with 200 millimeter× 20 millimeter Generator head at about 17,500 rpm for about 1 minute, then at about 24,000 rpm for about 5 minutes.

The emulsion was then titrated with about 3% citric acid solution until the pH reached about 3.8. Then, about 15 g SiO2 (Flo Guard FF, average size of about 18 micrometers) was added in and allowed to mix for about 30 minutes. The slurry was then filtered by pouring over a filter cloth with greater than about 5 micrometers holes. The particulates on the filter cloth were then resuspended into about 2000 g water containing about 0.5 g citric acid, about 0.5 g sucrose stearate (S-1570), and about 7.5 g SiO2 (Flo Guard FF). The slurry was mixed for about 15 minutes and then re-filtered. The washing was repeated one more time as above, then filter cake was collected. The filter cake was then pressed by placing in a 30 micrometers filter bag in a press box and squeezing in a cheese press at about 20 psi for about 20 minutes to remove more of the water. The press cake moisture was about 18.8%.

The press cake was mixed with about 50 g SiO2 (Flo Guard FF) in a 5 quart Hobart mixer with a whip at speed set at 1 for about 5 minutes. The material from the Hobart mixer was ground in a Fitz Mill Model DA SO6 Comminutor with hammers forward at the highest speed using a 1532-0020 perforated plate. The ground material was tumbled using jar tumblers for about 60 minutes. The batch was then dried in a Uni-Glatt Fluid Bed Dryer at about 40° C. for about 20 minutes. The dried batch was screened and only particles between 75-250 micrometers were collected. Note that the payload generally refers to the weight percentage of the encapsulated functional ingredients in relation to the final product. For this example, the total payload generally refers to the total weight percentage of all the encapsulated functional ingredients in relation to the final product.

|  | % alpha-Pinene | % para-Cymene | % Linalyl acetate | % Thymyl acetate | Total Payload |
|---|---|---|---|---|---|
| Payload | 0.84 | 2.70 | 1.50 | 6.40 | 11.44 |
| Surface Oils | <0.001 | 0.007 | 0.003 | 0.021 | 0.031 |

Example #11

Preparing a Powdered Beverage with Microencapsulated Material

Fruit flavored powdered beverages were purchased from a supermarket, and both orange and mango type were used to prepare a low pH powdered soft drink. Powdered soft drinks such as fruit based type are suitable for the delivery of enteric active compounds for several reasons: 1) The powdered drink can easily be dry blended with microencapsulated material, and provide shelf stability for extended period of time, 2) when reconstituted, the beverage has an acidic pH (similar to stomach pH), no early release, and, therefore, no adverse effect on taste, 3) Beverages, once prepared, are typically consumed within a very short period of time.

The orange type powdered beverage was sweetened with sugar and artificial sweetener and was dry blended with the microencapsulated essential oil from example #10. A single serve portion, such as about 7 g of orange powder, was dry blended with about 0.48 g of microencapsulated powder (active payload=about 11.44 percent), the amount selected to provide the desired functional benefit of the microencapsulated hydrophobic liquid. Additionally 0.35 g of carboxy methyl celluolose (Aqualon 7HXF) was added to the dry blend to provide extra viscosity and better suspendability. The dry blend was reconstituted into about 200 ml of cold water. The beverage was tasted after about 5 and about 60 minutes after reconstitution by an informal sensory panel. Testing by a sensory panel demonstrated successful masking of the essential oil blend in the orange type beverage.

A similar evaluation was made with mango type beverage with similar results.

Example #12

A Coated, Microencapsulated Product was Prepared Including an Essential Oil Blend Having an Enteric Matrix Combination of Shellac and Caseinate The matrix solution was prepared in two parts. First, a shellac solution including about 480 g of a 25% shellac solution was diluted with about 1600 g of DI water. The 25% shellac stock solution was pre-prepared ahead of time. The pH of the solution was about 7.5. Next, a caseinate solution was prepared with an overhead mixer. In particular, about 180 g of sodium caseinate was hydrated in about 1800 g DI water. Mixing was carried out at low speed until all powder was completely hydrated. The caseinate solution was then slowly added to the shellac solution under gentle mixing resulting in a final pH of about 7.3.

Next, about 100 g of an essential oil blend (about 70% Thymyl Octanoate, about 15% Linalyl acetate, about 10% para-cymene, about 5% alpha-pinene) was added slowly to the mixed solution. Once all the oil was added, high shear (rotor and stator type) was applied to prepare a coarse emulsion. The coarse emulsion was then high pressure-homogenized using a dual stage homogenizer at about 500 psi and about 5000 psi (first and second stage respectively) to provide a fine emulsion.

Next, the fine emulsion was titrated using about a 12% citric acid solution while mixing. Titration of the fine emulsion continued until the pH reached about 4.5, at which time most of the emulsified particulates were precipitated out with the actives entrapped within. The particulates were filtered out using filter press at about 40 psi for about 30 minutes to form a filter cake. The cake was then pulverized in a food processor. The pulverized particulates were fluid bed dried (pre dried) at about 60 degrees C. for about 10 minutes, then fine ground using a 0.75 millimeter screen. The final grind was dried at about 60 degrees C. for about 40 minutes. The next day, the particulates were further dried at about 40 degrees C. for about 20 minutes. Dried particulate was sifted and the fraction between 75 and 200 micrometers was collected.

The sifted, dried particulate was then further coated. First, about 200 g of base, uncoated particulate was added to a fluidized bed (Mini-Glatt) and warmed to about 40 C for about 15 minutes. Next, two coating solutions were prepared. The first solution was about 22.5 g of zein, about 2.5 g Sorbitol and about 130 g water. While mixing the slurry, ammonium hydroxide was added until the pH increased to about 9.5. Next, sodium hydroxide was added until the pH increased to about 10.5. Sufficient water was added to reach about 15% solids in the first solution. After the uncoated material was fluidized for about 15 minutes, the first solution was pumped into the 0.8 millimeter atomizing nozzle at about 1.2 g/minute with an atomization pressure of about 2 bars. After the first solution was pumped into the Mini-Glatt, the unit was stopped to clean the nozzle and restarted at about 40 C.

Next, a second solution including about 90 g of about 25% shellac solution, about 2.5 g sorbitol and about 74.2 g water was prepared and mixed until the sorbitol was fully dissolved. The second solution (shellac/sorbitol) was then pumped into the 0.8 millimeter atomizing nozzle at about 1.1 g/minute with an atomization pressure of about 2 bars. After the second solution was added, the particles were left to fluidize for about 10 minutes at about 40 C to fully dry them. The coated particles were then sieved to about 75 to about 200 micrometers and submitted for payload and surface/free oil analysis shown below. Note that the payload generally refers to the weight percentage of the encapsulated functional ingredients in relation to the final particulate product. For this example, the total payload generally refers to the total weight percentage of all the encapsulated functional ingredients in relation to the final particulate product. The total surface oil generally refers to the weight percentage of functional ingredients on the surface of the particles in relation to the final particulate product weight.

| | % alpha-Pinene | % para-Cymene | % Linalyl acetate | % Thymyl Octonoate | Total Payload |
|---|---|---|---|---|---|
| Payload | 0.78 | 1.4 | 2.2 | 12.8 | 17.5 |

Total Surface Oils = 0.5%

Example #13

Preparation of Powder Beverage with Coated Microcapsules

Coated microencapsulated essential oil powder from Example 12 was dry blended with a fruit flavored powder beverage (Orange flavor & Mango). The powder beverage was then sweetened with both sugar and an artificial sweetener. More particularly, a single serving amount of about 7 g of powder beverage was dry blended with 0.5 g of the coated microencapsulated essential oil powder. The powder was then hydrated in about 200 ml of cold water. The product was sensory evaluated by an informal sensory panel (12 people). The informal sensory panel reported that the beverage had a very refreshing fruity and tangy taste with no noticeable off flavor. The product was also tasted after about 30 and about 45 minutes, with no change in flavor profile.

Example #14

Stability of Capsules Over Shelf Life

Coated microencapsulated essential oil powder from Example 12 was packaged into foil type packaging. In particular, about 15 grams of coated microencapsulated essential oil powder were includes in each foil-type pouch. The pouches were heat sealed and then stored at either refrigerated temperatures (about 5 C) or in accelerated storage chamber (about 32 C and about 80% RH). The coated microencapsulated essential oil powder was taken out of storage at different time intervals (every 2 weeks) for sensory and analytical evaluation. For taste evaluation, the coated microencapsulated essential oil powder was dry-blended with a powder beverage as described in Example 13. The dry-blended mixture was then hydrated in water to produce a beverage product. The beverage product was tasted by the same informal panel. The resulting beverage products (were acceptable (i.e., no off flavor, and having a pleasant and refreshing taste as compared to a beverage without the coated microencapsulated essential oil powder) after the coated microencapsulated essential oil powder was stored for up to about 12 weeks of accelerated shelf life (with one week in accelerated storage believed to be equivalent to one month at ambient storage). Additionally, the prepared beverage product was analyzed for active ingredient within the beverage product that might have leaked out of the microcapsules. The tests showed a change of less than 1 ppm of active ingredient within the beverage products during the duration of the study. This very low level of free active ingredient did not have an impact on the product sensory attributes.

Example #15

In Vitro Testing of Simulated Release in Stomach and Small Intestine

Coated microencapsulated essential oil powder from Example 12 was treated into simulated In Vitro. Release from enteric microcapsules was evaluated by sequential simulation in stomach simulation solution (about 10 mg/ml pepsin, about 2 mg/ml NaCl, pH about 2) for about 30 min followed by small intestinal simulation solution (about 10 mg/ml pancreatin, about 2.4 mg/ml bile salt, pH about 6.8) for up to about 24 hr at about 37 C. Samples were taken at pre-determined time intervals and analyzed for release of individual actives.

FIG. 8 illustrates the enteric release properties of the matrix. A minimum release was observed during the first 30 minutes of digestion at a pH below about 4 in simulated stomach conditions. The observed release increased up to about 70% within about 3 hours of digestion in simulated intestinal conditions. Release continued in simulated intestinal conditions to about 90% after about 25 hours.

While the methods and compositions have been particularly described with specific reference to particular process and product embodiments, it will be appreciated that various alterations, modifications, and adaptations may be based on the present disclosure, and are intended to be within the spirit and scope of the invention as defined by the following claims.

What is claimed is:

1. A method of microencapsulating an active ingredient with an enteric matrix, the method comprising:
   a) agitating a combination of water and enteric materials, the combination substantially free of organic solvents, at a pH so that the enteric materials are soluble in the water to form a solution, the enteric materials including shellac and sodium caseinate;
   b) mixing a hydrophobic liquid containing the active ingredient into the solution;
   c) homogenizing the hydrophobic liquid and the solution to create an emulsion; and
   d) acid titrating the emulsion with an amount of acid to a pH at about an isoelectric point of sodium caseinate effective to precipitate a particulate of a plurality of hydrophobic liquid drops homogenously dispersed throughout an enteric matrix of the shellac and sodium caseinate.

2. The method of claim 1 wherein the enteric materials consist essentially of shellac and sodium caseinate.

3. The method of claim 2 wherein the shellac and sodium caseinate are provided in a ratio from about 90:10 to 10:90.

4. The method of claim 3 wherein the ratio of shellac to sodium caseinate is from about 30:70 to 70:30.

5. The method of claim 3 wherein the ratio of shellac to sodium caseinate is from about 40:60 to 60:40.

6. The method of claim 1 wherein the enteric materials are food grade.

7. The method of claim 1 further comprising applying an outer coating to the microencapsulated particulate precipitate by:
   e) blending an enteric coating material and a plasticizer to form a combination; and f) coating the microencapsulated particulate precipitate with the combination to provide a coated microencapsulated particulate precipitate.

8. The method of claim 7 including the steps:
g) providing a second combination of a second enteric coating material and a plasticizer; and
h) coating the coated microcapsulated particulate precipitate with the second combination.

9. The method of claim 8 wherein the second enteric coating material is shellac.

10. The method of claim 7 wherein the combination includes plasticizer in an amount ranging between about 1 percent to about 3 percent by weight and enteric coating material in an amount ranging between about 5 to about 20 percent by weight.

11. The method of claim 7 wherein the enteric coating material is selected from the group consisting of zein, shellac, and mixtures thereof.

12. The method of claim 7 wherein the enteric coating material is zein.

13. The method of claim 1 wherein the plasticizer is a sugar alcohol.

14. The method of claim 13 wherein the sugar alcohol is sorbitol.

15. The method of claim 1 further comprising (d1) filtering, washing and drying the particulate precipitate to produce a dry powder.

16. The method of claim 1 further comprising (a1) adding a base in an amount effective to maintain the pH between about 7 to about 12.

17. The method of claim 16 wherein the base is sodium hydroxide.

18. The method of claim 16 wherein the base is ammonium hydroxide.

19. The method of claim 1 wherein the hydrophobic liquid is selected from the group consisting of essential oils, triglycerides, unsaturated and polyunsaturated fatty acids, unsaturated and polyunsaturated lipids, beta-carotene, oil soluble vitamins and mixtures thereof.

20. A microencapsulated particulate composition comprising:
a hydrophobic liquid;
a matrix comprising an enteric material including shellac and sodium caseinate microencapsulating a plurality of drops of the hydrophobic liquid homogenously dispersed throughout the matrix; and
a coating around the matrix, the coating including a combination of a plasticizer and an enteric coating material for covering the enteric matrix.

21. The composition of claim 20 wherein the shellac and sodium caseinate are provided in a ratio from about 90:10 to 10:90.

22. The composition of claim 21 wherein the ratio of shellac to sodium caseinate is from about 30:70 to 70:30.

23. The composition of claim 21 wherein the ratio of shellac to sodium caseinate is from about 40:60 to 60:40.

24. The composition of claim 20 wherein the enteric material consists essentially of sodium caseinate and shellac.

25. The composition of claim 20 including a second coating composition for covering the coating and including a combination of a second enteric coating material and a plasticizer.

26. The composition of claim 20 wherein the coating combination includes plasticizer in an amount ranging between about 1 percent to about 3 percent by weight and enteric material in an amount ranging between about 5 to about 20 percent by weight.

27. The composition of claim 20 wherein the plasticizer is a sugar alcohol.

28. The composition of claim 27 wherein the sugar alcohol is sorbitol.

29. The composition of claim 20 wherein the hydrophobic liquid is selected from the group consisting of essential oils, triglycerides, unsaturated and polyunsaturated fatty acids, unsaturated and polyunsaturated lipids, beta-carotene, oil soluble vitamins and mixtures thereof.

30. The method of claim 1 further comprising the steps of coating the particulate precipitate with a first coating comprising zein and then coating the particulate precipitate with a second coating comprising shellac.

31. The method of claim 1 wherein the particulate precipitate has a particle size of about 1 to about 1000 µm.

32. The method of claim 1 wherein the shellac and sodium caseinate cross-link to form the matrix.

33. The composition of claim 20 wherein the coating around the matrix comprises a first coating including zein and a second, outer coating including shellac.

34. The composition of claim 20 wherein the particulate composition has a particle size of about 1 to about 1000 µm.

35. The composition of claim 20 wherein the shellac and sodium caseinate cross-link to form the matrix.

\* \* \* \* \*